United States Patent [19]

Hathman

[11] Patent Number: 5,086,763
[45] Date of Patent: Feb. 11, 1992

[54] PROTECTIVE RECLOSABLE WOUND DRESSING

[76] Inventor: Johnnie L. Hathman, 1310 Summertime La., Culver City, Calif. 90230

[21] Appl. No.: 562,831

[22] Filed: Aug. 6, 1990

[51] Int. Cl.⁵ ............ A61F 13/00; A61F 15/00; A61L 15/00
[52] U.S. Cl. ................... 602/42; 128/887; 128/888; 602/79
[58] Field of Search ............ 128/155, 887, 888; 604/307

[56] References Cited

U.S. PATENT DOCUMENTS

| | | |
|---|---|---|
| 679,918 | 8/1901 | Shears . |
| 697,637 | 4/1902 | Lee . |
| 1,920,808 | 8/1933 | Sander .................... 604/307 |
| 2,367,690 | 1/1945 | Purdy . |
| 3,026,874 | 3/1962 | Stevens . |
| 3,334,626 | 8/1967 | Schimmel . |
| 3,888,247 | 6/1975 | Stenvall . |
| 3,954,105 | 5/1976 | Nordby et al. . |
| 4,399,816 | 8/1983 | Spangler ................. 128/888 |
| 4,470,410 | 9/1984 | Elliot . |
| 4,709,695 | 12/1987 | Kohn et al. . |
| 4,909,243 | 3/1990 | Frank et al. ............ 128/155 |
| 4,926,883 | 5/1990 | Strock .................... 128/888 |
| 4,972,829 | 11/1990 | Knerr .................... 128/155 |

Primary Examiner—Randall L. Green
Assistant Examiner—Paul Prebilic
Attorney, Agent, or Firm—Paul H. Ware

[57] ABSTRACT

A disposable, protective reclosable wound dressing or bandage providing wound access that is easy to apply and/or open without disturbing a protective crust of blood and serum that forms over a wound, said crust being more commonly called a scab. In addition, it is convenient to apply medication without removing the bandage and at the same time, the wound may be inspected and otherwise treated while maintaining the bandage in place. The dressing is low in cost, simple and uncomplicated, non-metallic and not rigid but resilient and thus adaptable to the shape of the body part to which it is applied. One of its most important features is its capability to be repeatedly opened for inspection or for the application of medication and thereafter to be reclosed without losing any of the integrity of seal.

3 Claims, 2 Drawing Sheets

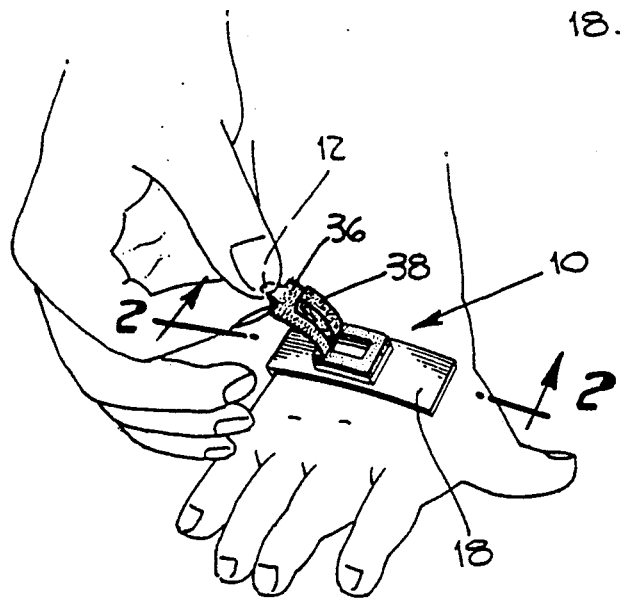
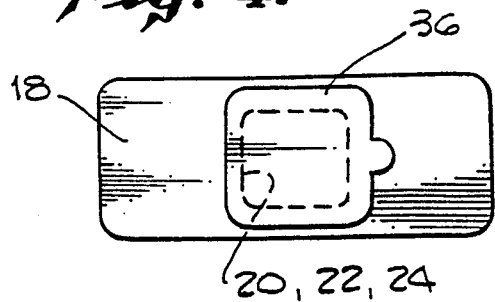
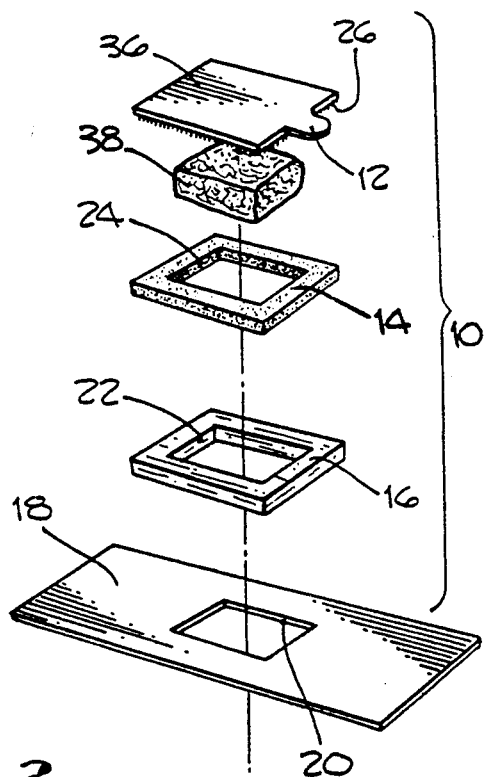
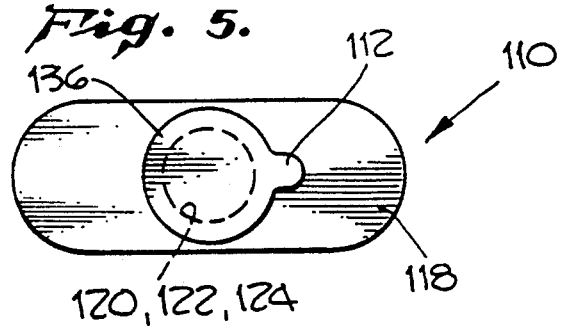
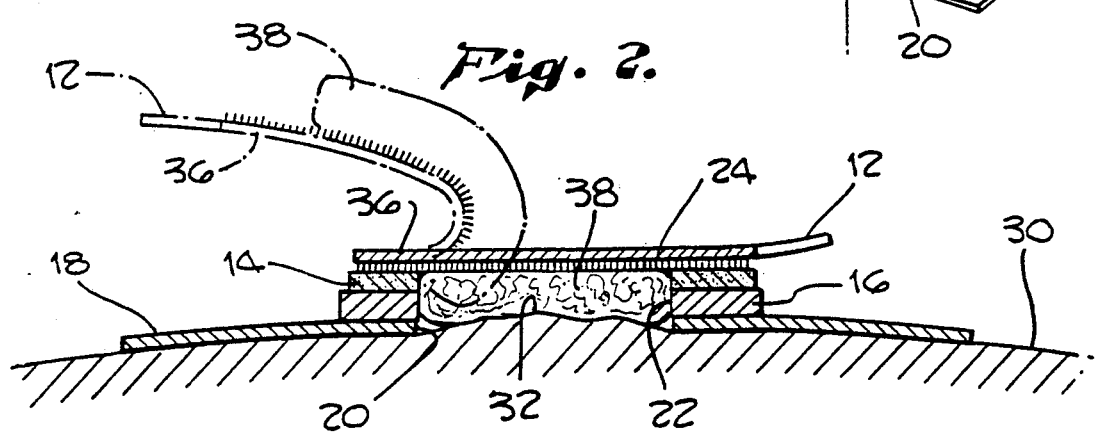

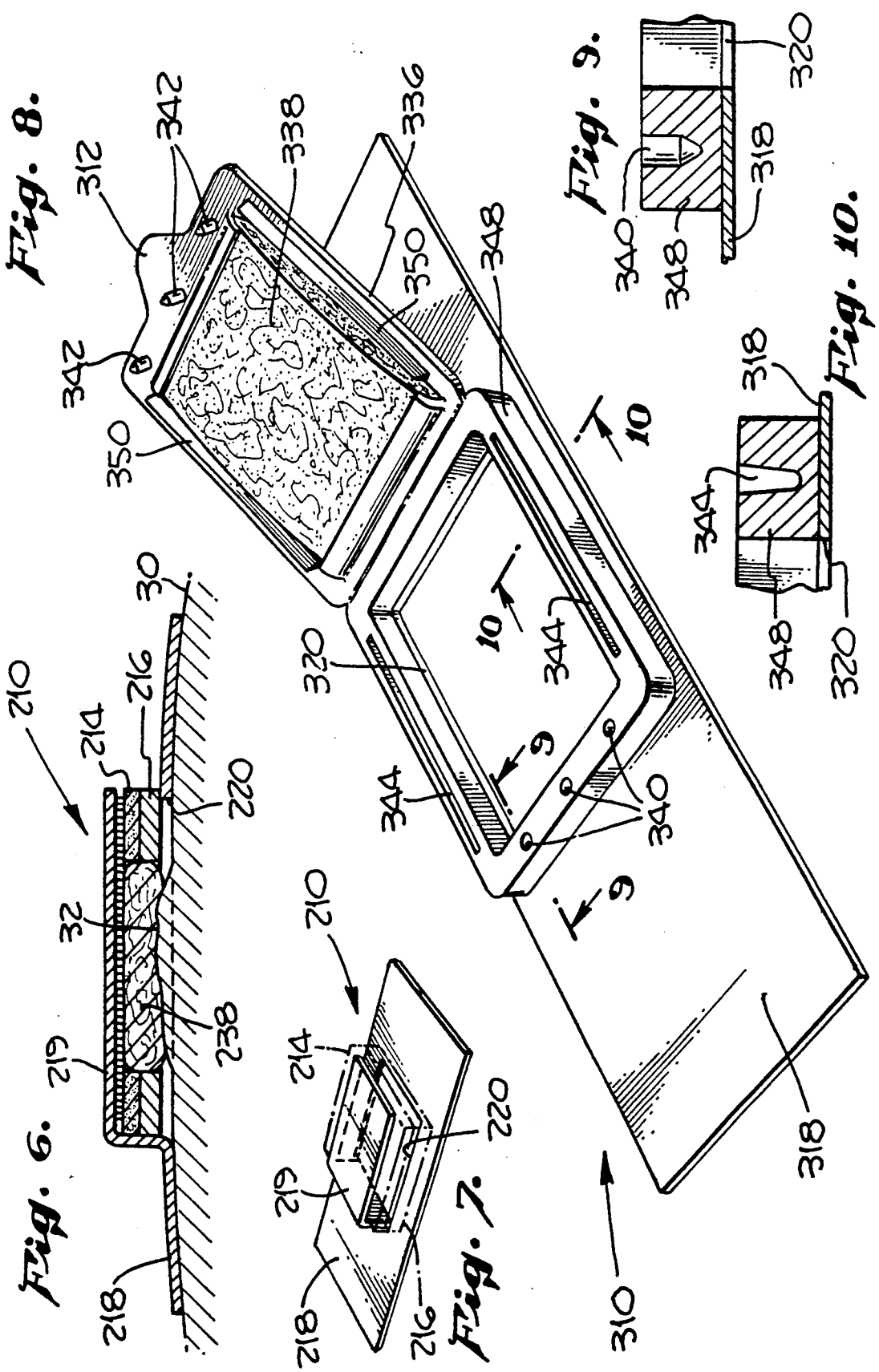

PROTECTIVE RECLOSABLE WOUND DRESSING

BACKGROUND OF THE INVENTION

1. Field of the Invention

This invention relates generally to disposable surgical dressings or bandages of inexpensive character but that nevertheless provide a protective dressing for minor injuries and that provide easy access to the injury during the time of the healing process for purposes of inspection, medication and cleaning or for other purposes. After opening the dressing for inspection, medication or for other purposes, the dressing may be reclosed without degradation of its protective capacity.

2. Description of the Related Art

Surgical dressings and bandages are known in which some attempt has been made to effectuate such advantages as are found in the present invention such as easy removability, convenient inspection and medication, non-degradable reclosure and so forth. These prior art devices have generally fallen short of creating the essence of a device sought to be implemented. Many different dressings or bandages have been devised in the attempts to solve the problems presented. Most have either presented new problems or only partially solved these problems or both.

In particular, the prior art dressings have not provided ready access to a wound or sore so as to permit medication and inspection from time to time as necessary without requiring removal of the entire dressing and the application of a new one. For example, in most of the prior art disposable bandages, the protective crust of blood and serum that forms over a wound, more commonly called a scab, would be found to have affixed itself to the part of the bandage forming a contact with the wound itself and upon removal of the bandage, that scab would adhere thereto thus removing itself from the wound and thereby making it necessary for the healing process to start over again, and, in the process, causing pain and anxiety to the bearer of the wound. In the present invention, such intimate contact with the wound may be prevented, thus there need not be removal of the scab and no consequent pain to the bearer of the wound.

Most of these prior art dressings or bandages have thus met special needs as presented by specific problems and have, therefore, served narrow purposes. These prior art devices, among other disadvantages, have been unreliable and unpredictable in operation under continued use and, even though some have been inexpensive and uncomplicated to manufacture and use, they have not served the purposes for which they were intended.

Some of these prior art devices were brought to the attention of the applicant through a novelty search conducted in the United States Patent and Trademark Office. These patents have been listed in the accompanying INFORMATION DISCLOSURE STATEMENT and PTO-1449.

The patent numbered U.S. Pat. No. 679,918, issued Aug. 6, 1901, to E. C. Shears, entitled SHIELD FOR WOUNDS, describes a non-disposable device comprising rigid frames hinged together having wire gauze for the covers and not providing the facility of adhesive attachment to the body. Compared to applicant's innovation, this device, though well attuned to its intended purpose, is cumbersome and heavy and probably quite a bit more expensive.

The patent numbered U.S. Pat. No. 697,637, issued Apr. 15, 1902, to J. E. Lee, entitled SHIELD FOR VACCINATIONS &c, describes a device that is rigid and fabricated of a material such that ventilation openings are required and having a stated purpose of protecting vaccinations, boils, carbuncles and the like. The device does not, nor is it intended to, reach the application sought to be fulfilled by applicant's invention. The device is also apparently quite expensive and complicated compared to applicant's invention.

The patent numbered U.S. Pat. No. 2,367,690, issued Jan. 23, 1945, to E. H. Purdy, entitled WOUND PROTECTOR, has a hard, transparent cover hinged to another member and appears to be expensive and complicated to manufacture. It does not seem to be a disposable device and thus, among other reasons, does not reach applicant's intended applications.

The patent numbered U.S. Pat. No. 3,026,874, issued Mar. 27, 1962, to R. C. Stevens, entitled WOUND SHIELD, has as its primary object the provision of a controlled drainage for a wound. The device is characterized as easily sterilized thus inferring non-disposability and expensive fabrication. This device is entirely different from applicant's invention and is directed at an entirely different application.

The patent numbered U.S. Pat. No. 3,954,105, issued May 4, 1976, to Nordby et al., entitled DRAINAGE SYSTEM FOR INCISIONS OR WOUNDS IN THE BODY OF AN ANIMAL, is directed, as the title implies, to a drainage system rather than a bandage. The device described is complicated and apparently quite expensive and further, entirely different from applicant's.

The patent numbered U.S. Pat. No. 4,470,410, issued Sept. 11, 1984, E. M. Elliot, entitled PROTECTIVE RETAINING DEVICE AND METHOD, appears to be very complicated and very expensive to manufacture. The primary purpose of the described device appears to be for application to the site of an intravenous or catheter intervention system. The stated purpose appears very different when compared to the purpose of the device applicant seeks to patent.

The patent numbered U.S. Pat. No. 3,334,626, issued Aug. 8, 1967, to M. M. Schimmel, entitled INJURY PROTECTION, does not provide a self-contained adhesive attachment for the device and does not provide easy accessibility for inspection, medication or for other purposes.

The patent numbered U.S. Pat. No. 3,888,247, issued June 10, 1975, to C. B. Stenvall, entitled FIRST AID BANDAGE, provides that the "lightly adhered microporous breathable surgical tape" that is first placed over the wound, shall be left in contact with the wound until after healing is completed. Thus, neither inspection or medication among other things, has been contemplated in contrast to applicant's invention.

The patent numbered U.S. Pat. No. 4,709,695, issued Dec. 1, 1987, to Kohn et al., entitled PROTECTIVE DEVICE, contemplates a device expected to be prepared by cutting to size for each case encountered. In the case of the eye covering embodiment, the protective covering is described as a semi flexible transparent covering. In another embodiment concerning a sutured lesion, multiple pieces of adhesive base are arranged about an L-shaped suture and a protective covering is cut by the care provider to fit the sutured lesion. While suitable for its intended purpose, this device is very different from applicant's device.

It would thus be a great advantage to the art to provide a disposable, protective bandage capable of allowing inspection of a wound without removal.

Another great advantage would be found in a disposable, protective bandage designed so that during the inspection of a wound, removal of a formed scab would be most unlikely.

An additional advantage would be realized by the provision of a disposable, protective bandage that provides easy access for purposes of the application of medication to a wound.

A further important advantage would be derived by the provision of a dressing that may be opened for inspection, medication or for other purposes and then reclosed without degradation to the sealing thereof.

A still further advantage to the art would be established by the provision of a disposable, protective bandage that would be acceptable to young children who may be frightened by the prospect of removal of a bandage that has adhered to a wound or sore.

Another significant advantage to the art would be characterized by the provision of a bandage exhibiting all of the previously mentioned advantages that is also quick and easy to apply and just as quick and easy to remove.

It would be a further desirable advantage to provide such a device embodying the advantages set forth above in a design and article that is economical and uncomplicated to manufacture.

SUMMARY OF THE INVENTION

It is the purpose of the present invention to provide for the above-stated desired advantages, thus a paramount object of the present invention is to provide a good disposable, protective bandage capable of allowing inspection of a wound without removal of the bandage and to provide thereafter for reclosure thereof without suffering degradation of the sealing capabilities of the dressing.

It is a further specific object to provide a disposable protective bandage designed so that during the inspection of a wound, removal of a formed scab would be most unlikely.

An additional notable object of the invention is to provide a disposable protective bandage that permits easy access to a wound for purposes of the application of medication.

An important object of the invention is realized by the design of a disposable, protective bandage that is acceptable to young children.

In the accomplishment of these and other objects a disposable, protective bandage has been fashioned comprising all the above objects and that is quick and easy to apply and just as quick and easy to remove.

The present invention embodies a device that is economical and uncomplicated to manufacture.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings wherein like reference characters refer to like parts throughout and in which:

FIG. 1 is a perspective view of the Protective Reclosable Wound Dressing showing it as a disposable bandage applied by a care provider to an injury and opened for inspection of the wound without removal of the bandage and illustrating its reclosable facility.

FIG. 2 is an enlargement cross sectional view taken along the sight lines 2—2 of FIG. 1.

FIG. 3 is an exploded view showing the constituent components of the device as they might be gathered for assembly.

FIG. 4 is a plan view of a preferred embodiment of the device.

FIG. 5 is a plan view of an alternate embodiment of the device.

FIG. 6 is a cross sectional view of an alternate embodiment of the device in which the covering flap is fabricated integrally with the adhesive tape used to adhere the dressing to the body.

FIG. 7 is a phantom perspective view showing the parts of FIG. 6 in phantom.

FIG. 8 is a perspective view of yet another embodiment in which the covering flap is secured by a different means and which may be used for a larger wound or injury which may require the closure after opening to be more precise.

FIG. 9 is an enlarged detail view taken along the sight lines 9—9 of FIG. 8.

FIG. 10 is an enlarged detail view taken along the sight lines 10—10 of FIG. 8.

DETAILED DESCRIPTION

Although specific embodiment of the invention will now be described with reference to the drawings, it should be understood that such embodiments are by way of example only and merely illustrative of but a small number of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

Referring now to FIG. 1 with greater particularity, there is shown a perspective view of the disposable protective, reclosable wound dressing after having been applied by a care provider to an injury on the back of a hand. The bandage may be applied to any part of the body and its application to a hand is merely for illustrative purposes and is not to be considered limiting or restricting with respect to the generality of this specification. The device is denoted generally by the numeral 10 and has been shown with its removable, inspection, medication, covering flap 36 held in the open position by the care provider by means of the tab 12. It is, of course, this position that permits open inspection of the wound being protected and the cleaning thereof and the application of medication thereto without necessitating complete removal of the flap 36. A gauze pad 38 that may be medicated, is shown in place on the flap 36 while the device is shown as secured to the back of the patient's hand by means of adhesive tape 18.

FIG. 2 is a cross-sectional view showing the parts of the device as assembled with the flap 36 closed and also, in phantom, opened. The adhesive tape 18, used for adhering the device to the body part denoted here by numeral 30, may be of any of the common types of surgical tape in wide use for that purpose. The tape 18 has an opening 20 of such dimension that the wound is fully contained or circumscribed within that opening and is, therefore, not contacted by the tape 18. A scab 32 has been shown therewithin illustrating the advantage that the wound and any formed scab will not be harmfully disturbed on account of the device by the inspection or application of medication thereto. The gauze pad 38 may or may not be introduced into the dressing at the discretion of the care provider. By the same token, the gauze pad 38 may be medicated and may be introduced after formation of the scab but before complete healing has been accomplished. A soft pad frame 16, having an opening 22 in registry with the opening 20 of tape 18 is affixed to the tape 18 so as to provide an outward offset therefrom and from the wound and its scab 32. Secured to soft frame 16, there is a pad frame 14 having an opening 24 in registry with opening 20 and 22 of tape 18 and soft pad frame 16 respectively and fabricated from a fabric of the kind used to adhere to a micro hook material as is utilized in a Velcro (tm) system being, as is well known in the art, a fastening system having a first surface fabricated from a micro hook material and an opposing surface fabricated from a fuzz or felt material or another material which adheres to said micro hook material by means of becoming ensnared by said micro hook material. The micro hook material utilized on one side of the removable, inspection, medication, covering flap 36 has been denoted by the numeral 26, (FIG. 3) such micro hook material providing easy attachability and detachability of said flap, and, if desired, only partial removal for purposes of inspection or medication as is illustrated. Thus the protective dressing may easily be opened by means of the tab 12 for whatever purpose required and just as easily reclosed without loss of integrity of the closure.

Referring now to FIG. 3, an exploded view permits examination of constituent parts of the bandage. As in FIG. 2, the adhesive tape 18 has an opening 20. The soft pad frame 16 has an opening 22 that will be in registry with opening 20 upon assembly. Pad frame 14 that provides the securing facility for the flap 36 has an opening 24 that will be in registry with both openings 20 and 22 upon assembly. Micro hook material 26 on the underside of flap 36 provides the access cover security for the device. It is also apparent that a gauze pad 38 that may or may not be medicated may be adhered to the underside of flap 36. Upon lifting the tab 12 the gauze pad 38 will adhere to the flap 36. The flap 36 is of such dimension as to effect complete coverage of the opening in the pad frame 14. Tab 12 provides operating means by which a care provider may operate the flap to its open or closed position. The micro hook attachment facility also permits easy complete removal and replacement of the flap 36, if so desired.

FIG. 4 depicts the device in plan view elevation with the openings 24, 22 and 20 in phantom. The adhesive tape 18 and the flap 36 are shown as essentially rectangular in shape.

FIG. 5 illustrates an alternative shaped embodiment of the protective, reclosable wound dressing 110 to indicate that the shape of the adhesive tape, denoted here by the numeral 118, openings, denoted in this figure by the numerals 124, 122 and 120, the flap 136 and the tab 112 need not be of any particular contour. These elements are shown here for purposes of illustration only, as essentially circular. It is intended, therefore, to show that the openings may be of any contour whatsoever.

FIG. 6 illustrates another embodiment of the wound dressing 210 wherein the covering flap takes the form of an elongated flap 219 formed integrally with the adhesive tape material 218. The pad frame 214 and the soft pad frame 216 perform the same functions as 14 and 16 of FIG. 3. The numeral 220 denotes the opening in adhesive tape 218 that is denoted in adhesive tape 18 by the numeral 20.

FIG. 8 depicts an embodiment of the wound dressing 310 in which the closure facility may be required to be more precise than in the foregoing embodiments. The adhesive tape 318 carries affixed thereto a locator pad frame 348 and has an opening in said tape denoted by the numeral 320 to circumscribe the wound. The locator pad 348 has hinged to it a flap 336 that may carry a gauze pad 338 which may or may not be medicated and may be applied, if desired, at any stage of healing of the wound as the care provider sees fit. As in the previously described embodiments, flap 336 has a tab 312 that is used to operate the opening and closure of the flap 336. Flap 336 further has fabricated thereupon locator pegs 342 at one end thereof and locator tongues 350 alongside each underside thereof. Locator pad frame 348 has fabricated therein locator holes 340 placed so as to accept locator pegs 342 located on flap 336 and in the same manner, locator pad frame 348 has fabricated therein locator grooves 344 placed so as to accept locator tongues 350 located on flap 336.

FIG. 9 shows an enlargement and detail of the locator holes 340 as fabricated in the locator pad frame 348 as attached to adhesive tape 318. The locator hole detail is shown in its relation to the opening 320 in the adhesive tape 318.

FIG. 10 shows an enlargement and detail of the locator grooves 344 as fabricated in the locator pad frame 348 as attached to adhesive tape 318. The locator groove detail is shown in its relation to the opening 320 in the adhesive tape 318.

Thus, there has been described a Protective Reclosable Wound Dressing providing wound access that offers enhancement to the art. Great improvements in accessibility to injuries, application of medication to injuries, ease of use and economy have been shown through the advantages of the invention.

It is pointed out that although the present invention has been shown and described with reference to particular embodiments, nevertheless, various changes and modifications, obvious to those skilled in the art to which the invention pertains, are deemed to lie within the purview of the invention.

ABSTRACT OF THE DRAWINGS

In the drawings, the numbers refer to like parts and, for the purpose of explication, set forth below are the numbered parts of the names of the elements of this invention.

| IDENTIFYING NUMERAL | NAME OF ELEMENT | SHOWN IN FIGS. |
| --- | --- | --- |
| 10 | Device generally | 1, 3 |
| 110 | Device generally | 5 |
| 210 | Device generally | 6, 7 |
| 310 | Device generally | 8 |
| 12 | Tab | 1, 2, 3 |
| 112 | Tab | 5 |
| 312 | Tab | 8 |
| 14 | Pad Frame | 2, 3 |
| 214 | Pad Frame | 6, 7 |
| 16 | Soft Pad Frame | 2, 3 |
| 216 | Soft Pad Frame | 6, 7 |
| 18 | Adhesive Tape | 1, 2, 3, 4 |
| 118 | Adhesive Tape | 5 |

-continued

| IDENTIFYING NUMERAL | NAME OF ELEMENT | SHOWN IN FIGS. |
|---|---|---|
| 219 | Adhesive Tape | 6, 7 |
| 318 | Adhesive Tape | 8, 9, 10 |
| 20 | Opening in Tape | 2, 3, 4 |
| 120 | Opening in Tape | 5 |
| 220 | Opening in Tape | 6, 7 |
| 320 | Opening in Tape | 8, 9, 10 |
| 22 | Opening in Soft Frame | 2, 3, 4 |
| 122 | Opening in Soft Frame | 5 |
| 24 | Opening in Pad Frame | 2, 3, 4 |
| 124 | Opening in Pad Frame | 5 |
| 26 | Micro Hook Material | 3 |
| 30 | Body Surface | 2, 6 |
| 32 | Scab or Wound | 2, 6 |
| 36 | Flap | 1, 2, 3, 4 |
| 136 | Flap | 5 |
| 336 | Flap | 8 |
| 38 | Gauze Pad | 1, 2, 3 |
| 238 | Gauze Pad | 6 |
| 338 | Gauze Pad | 8 |
| 340 | Locator Holes | 8, 9 |
| 342 | Locator Pegs | 8 |
| 344 | Locator Grooves | 8, 10 |
| 348 | Locator Pad Frame | 8, 9, 10 |
| 350 | Locator Tongue | 8 |

What is claimed and desired to be secured by Letters Patent of the United States is:

1. A disposable, protective, reclosable wound dressing bandage providing access to a wound, comprising:
   an adhesive tape for adhering said bandage to a body part, said tape having an opening such that the wound is circumscribed therewithin:
   a soft pad frame affixed to said adhesive tape and said soft pad frame having an opening in registry with said opening in said adhesive tape, said soft pad frame providing an outward offset from said adhesive tape;
   a pad frame secured to said soft pad frame, said pad frame having an opening in registry with said openings in said adhesive tape and in said soft pad frame, respectively, said pad frame being fabricated from a fabric used to adhere to a micro hook material;
   a gauze pad having dimensions such that said gauze pad fits within said openings in registry with said adhesive tape, said soft pad frame and said pad frame;
   a removable inspection, medication covering flap having micro hook material on a substantial portion of a side thereof for detachably securing said flap to said pad frame and to said gauze pad, said flap having a tab for use by a care provider so as to open, close and remove said flap.

2. The disposable, protective, reclosable wound dressing bandage of claim 1 wherein said opening in said adhesive tape may of any contour that permits circumscription of said wound;
   said opening in said soft pad frame in registry with said opening in said adhesive tape is of like contour as the opening in said adhesive tape;
   said opening in said pad frame in registry with said openings in said adhesive tape and in said soft pad frame, respectively, is of like contour as said openings in said adhesive tape and said soft pad frame.

3. The disposable, protective, reclosable wound dressing bandage of claim 2 wherein said opening in said adhesive tape is essentially circular;
   said opening in said soft pad frame in registry with said opening in said adhesive tape is essentially circular; and
   said opening in said pad frame in registry with said openings in said adhesive tape and in said soft pad frame, respectively, is essentially circular.

* * * * *